United States Patent [19]

Eberspach et al.

[11] Patent Number: 5,099,017
[45] Date of Patent: Mar. 24, 1992

[54] N,N'-BIS-1,3,5-TRIAZIN-6-YLPIPERAZINES, AND PROCESSES FOR THEIR PREPARATION

[75] Inventors: Werner Eberspach, Frankfurt am Main; Günther Lenz, Frechen; Manfred Lysek, Bonn, all of Fed. Rep. of Germany

[73] Assignee: Hoechst Aktiengesellschaft, Frankfurt am Main, Fed. Rep. of Germany

[21] Appl. No.: 564,409

[22] Filed: Aug. 8, 1990

[30] Foreign Application Priority Data

Aug. 22, 1989 [DE] Fed. Rep. of Germany ....... 3927623

[51] Int. Cl.$^5$ .................. C07D 251/52; C07D 403/14
[52] U.S. Cl. .................... 544/198; 544/113; 544/209; 544/212
[58] Field of Search ................ 544/198, 209, 212, 113

[56] References Cited

FOREIGN PATENT DOCUMENTS

| 0246483 | 11/1987 | European Pat. Off. |
| 8302943 | 9/1983 | PCT Int'l Appl. |
| 1448490 | 9/1976 | United Kingdom |
| 1511773 | 5/1978 | United Kingdom |

OTHER PUBLICATIONS

Geigy, AG/. Chemical Abstracts, vol. 59, entry 10088h (1963).
Agripat S.A. Chemical Abstracts, vol. 67, entry 12664r (1967).
Geigy, AG., Chemical Abstracts, vol. 72, entry 3511q (1970).
Ahne et al. Chemical Abstracts, vol. 82, entry 59007d (1975).

*Primary Examiner*—John M. Ford

[57] ABSTRACT

The invention relates to novel N,N'-bis-1,3,5-triazin-6-ylpiperazines of the formula

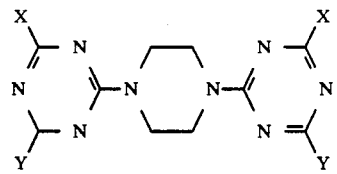

in which X and Y are identical or different radicals —$OR^1$, $SR^1$ or —$NR^2R^3$,
where
$R^1$ is a $C_1$- to $C_{18}$-alkyl group, a $C_5$- to $C_{18}$-cycloalkyl group, a phenyl or naphthyl group, or a $C_7$- to $C_{18}$-aralkyl group;
$R^2$ and $R^3$, independently of one another, are a $C_1$- to $C_3$-alkyl group, a $C_5$- to $C_{18}$-cycloalkyl group, a phenyl or naphthyl group, or a $C_7$- to $C_{18}$-aralkyl group, or
—$NR^2R^3$ are piperidinyl or morpholinyl.

In addition, 2 processes for the preparation of the novel substances are described.

16 Claims, No Drawings

N,N'-BIS-1,3,5-TRIAZIN-6-YLPIPERAZINES, AND PROCESSES FOR THEIR PREPARATION

The invention relates to novel N,N'-bis-1,3,5-triazin-6-ylpiperazines of the formula

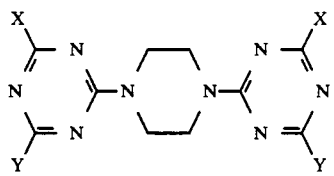

in which X and Y are identical or different radicals —$OR^1$, —$SR^1$ or —$NR^2R^3$, where $R^1$ is a $C_1$- to $C_{18}$-alkyl group, a $C_5$- to $C_{18}$-cycloalkyl group, a phenyl or naphthyl group which is optionally substituted by inert radicals, or a $C_7$- to $C_{18}$-aralkyl group;

$R^2$ and $R^3$, independently of one another, are a $C_1$- to $C_3$-alkyl group, a $C_5$- to $C_{18}$-cycloalkyl group, a phenyl or naphthyl group which is optionally substituted by inert radicals, or a $C_7$- to $C_{18}$-aralkyl group, or —$NR^2R^3$ is piperidinyl of the formula

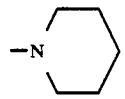

or morpholinyl of the formula

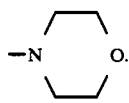

As amino-substituted triazine derivatives, the compounds according to the invention are chemically related to known herbicides such as 2-ethylamino-4-tert.-butylamino-6-methoxy-1,3,5-triazine, 2-methoxy-4,6-bis(isopropylamino)-1,3,5-triazine or 2-ethylamino-4-sec.-butylamino-6-methoxy-1,3,5-triazine, and can be used like these as chemical weed-control agents.

N,N'-Bis-1,3,5-triazin-6-ylpiperazines which are similar, but must contain at least one 2,2,6,6-tetramethylpiperidyl radical as substituents and are intended for use as agents for stabilizing polymers, and two different analogous processes for their preparation have already been described in DE 26 36 130 C3. Both of the processes described are two-step processes which involve isolation of the intermediates, or start from an already known intermediate which is reacted in a one-step reaction to give the target product.

In a similar manner, the invention also relates to two processes for the preparation of the novel N,N'-bis-1,3,5-triazin-6-ylpiperazines.

In process 1, cyanuric halide, preferably cyanuric chloride, is reacted in a first process step with piperazine to give N,N'-bis(2,4-dichloro-1,3,5-triazin-6-yl)piperazine (cf. DE 26 36 130 C3, Example 6A). In the second process step, substitution reactions of the intermediate with the compounds XH and YH give the bis-triazinylpiperazines according to the invention.

The first process step can be carried out, for example, by initially introducing cyanuric chloride in a suitable suspending agent and simultaneously adding aqueous solutions of piperazine and of a base with cooling. The addition is carried out in a manner such that the reaction temperature can be kept between −20° C. and 0° C. and the pH can be kept in the range from 5–7. The insoluble intermediate is filtered off, washed with water and employed in filter-moist form for the 2nd step.

In contrast to Example 6A of DE 26 36 130 C3, the first reaction step is preferably carried out in a 1:1 mixture (parts by weight) of ice and acetone as suspending agent. In order to scavenge the hydrogen chloride formed during the reaction, bases such as hydroxides, carbonates or bicarbonates of alkali metals or alkaline earth metals, but preferably $Na_2CO_3$, can be employed. The molar ratio between the base and cyanuric chloride is (1.2 to 1.0):1 in the case of monobasic bases such as NaOH and (0.6 to 0.5):1 in the case of dibasic bases such as $Na_2CO_3$. The amount of piperazine used is from 0.6 to 0.5 mol per mol of cyanuric chloride.

The second process step is generally carried out in different ways, depending on the compound XH and YH.

In the case where $X=Y=$—$OR^1$, the intermediate is suspended, for example, in an excess of the appropriate alcohol, preferably methanol or ethanol, or in a mixture of the alcohol with an inert solvent, and 2.2 to 2.0 mol of base are added per mol of cyanuric chloride. Suitable bases are, in particular, alkali metal hydroxides, which are dissolved in the appropriate alcohol or in an inert solvent. Due to the lack of solubility of the intermediate, it is in some cases advantageous to add 0.01 to 0.5% by weight (based on cyanuric chloride) of a phase transfer catalyst, such as tetra-n-butylammonium bisulfate as an additional component. The reaction mixture is refluxed for 12 to 20 hours and then filtered, and the residue is washed with water and dried.

In the case where $X=Y=$—$SR^1$ or —$NR^2R^3$, the filter-moist intermediate is suspended in water, and solutions of a base and of the particular thiol or amine are simultaneously added. The solvent used is water or a water-miscible liquid. However, thiols or amines which are liquid at room temperature can also be added dropwise in undiluted form. Suitable bases are hydroxides, bicarbonates or carbonates of alkali metals or alkaline earth metals, which are employed, based on the cyanuric chloride employed in the first step, in the molar ratio (2.2 to 2.0):1 (monobasic bases) or (1.1 to 1.0):1 (dibasic bases). The molar ratio between the thiol or amine and the cyanuric chloride employed in the first step is (2.2 to 2.0):1. The reaction mixture is refluxed for 12 to 20 hours and subsequently filtered, and the residue is washed with water and dried.

In the case where X is not identical with Y, the N,N'-bis-triazinylpiperazines according to the invention can be prepared by successive reactions of the intermediate with the compounds XH and YH. The reaction product from the first substitution is filtered off, washed with water and employed in filter-moist form for the second substitution. The reaction conditions in the first and second substitutions are analogous to those described above.

In the case where X is not identical with Y and X and/or $Y=$—$OR^1$, the molar ratio between the base and the cyanuric chloride employed in the first step is (1.1 to 1.0):1 in the case of monobasic bases such as NaOH and (0.55 to 0.5):1 in the case of dibasic bases such as $Na_2CO_3$.

In the case where X is not identical with Y and X and/or Y=—SR¹ or —NR²R³, the molar ratio between the particular thiol or amine and the cyanuric chloride employed in the first step is (1.1 to 1.0):1, and that of the base is (1.1 to 1.0):1 in the case of monobasic bases and (0.55 to 0.5):1 in the case of dibasic bases.

In process 2, the compounds according to the invention where X=Y can surprisingly be prepared in a 2-step one-pot synthesis. In this, the cyanuric halide, preferably cyanuric chloride of the formula

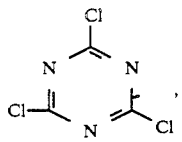

is disubstituted by a compound XH or YH in the presence of a base to scavenge the HCl, giving the intermediate of the formula

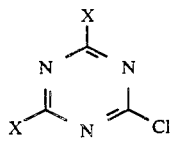

and this intermediate is reacted without prior isolation in the same reaction vessel with piperazine of the formula

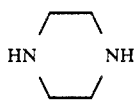

again in the presence of a base to scavenge the HCl, giving the target product.

For example, a mixture of a base, the particular compound XH or YH and in some cases a phase transfer catalyst is initially introduced, and cyanuric halide is added in such a manner that the reaction temperature does not exceed 30° C. and the pH is between 5 and 11. The reaction temperature is subsequently kept at the boiling point of the suspending agent for 30 to 40 minutes.

In the case where X=Y=—OR¹, the appropriate alcohol, preferably methanol or ethanol, is, for example, employed in excess since it is simultaneously used as the suspending agent in the form of a mixture of 9–11 parts by volume of alcohol and 1 part by volume of water or of an inert liquid.

In the case where X=Y=—SR¹ or —NR²R³, water or an inert liquid is used as the reaction medium; the molar ratio between the thiol or amine and cyanuric halide is then (2.2 to 2.0):1. Suitable bases are hydroxides, carbonates or bicarbonates of alkali metals or alkaline earth metals. The molar ratio between the base and cyanuric halide is (2.2 to 2.0):1 in the case of monobasic bases and (1.1 to 1.0):1 in the case of dibasic bases. A phase transfer catalyst which can be used is 0.1 to 1% by weight of tetra-n-butylammonium bisulfate, based on the amount of cyanuric halide employed.

In the second step of the one-pot process, aqueous solutions of piperazine and of a base are added to the reaction mixture which is refluxed for 2–18 hours. The bis-triazinylpiperazines, which are generally insoluble, are filtered off, washed with water and dried. The molar ratio between piperazine and the cyanuric halide employed in the 1st step is (1.2 to 1.0):2. Suitable bases are, in particular, Na₂CO₃ or alkali metal hydroxides, which are employed in the molar ratio (0.6 to 0.5):1 or (1.2 to 1.0):1 respectively, based on the cyanuric halide employed in the 1st step.

In detail, the present invention thus relates to a first process for the preparation of the novel N,N'-bis-1,3,5-triazin-6-ylpiperazines, wherein, in a first reaction step, cyanuric halide, piperazine and an inorganic base are reacted in the molar ratio 1:(0.5 to 0.6):(1 to 1.2) in the case of a monobasic base and in the molar ratio 1:(0.5 to 0.6):(0.5 to 0.6) in the case of a dibasic base, in the presence of water and in the presence of a further suspending agent, at temperatures of minus 20° C. to 0° C. and at a pH of 5 to 7, and the N,N'-bis(2,4-dichloro-1,3,5-triazin-6-ylpiperazine obtained as an intermediate is filtered off, washed with water and mixed, in a second reaction step, with a compound XH or YH and an inorganic base in the molar ratio (2 to 2.2):(2 to 2.2) per mol of the cyanuric halide employed in the first reaction step in the case of a monobasic base and in the molar ratio (2 to 2.2):(1 to 1.1) per mol of the cyanuric halide employed in the first reaction step in the case of a dibasic base, in the presence of a suspending agent, the mixture is refluxed for 12 to 20 hours, cooled and neutralized, and the target product is filtered off.

The first preparation process of the invention may optionally and preferably have the features that
a) a phase transfer catalyst, preferably 0.01 to 0.5% by weight of tetra-n-butylammonium bisulfate, calculated on the basis of the cyanuric chloride employed in the first step, is added to the second reaction step;
b) in the first reaction step, after addition of all the reaction components, the reaction mixture is stirred for up to 1 hour at temperatures not exceeding 0° C.;
c) in the case where X and/or Y=—OR¹, the suspending agent employed in the second reaction step is the corresponding alcohol, the corresponding phenol or naphthol, or a mixture thereof with water, acetone, dioxane, toluene or xylene;
d) in the case where X and/or Y=—SR¹ or —NR²R³, the suspending agent employed in the second reaction step is water or mixtures of water with acetone or dioxane;
e) acetone, dioxane, toluene or xylene is employed in the first reaction step as a further suspending agent;
f) in the case where X is not identical with Y, the intermediate is reacted in the second reaction step successively with the compounds XH and YH in the presence of the inorganic base in the appropriate molar ratios, the reaction product from the first substitution being filtered off, washed with water and employed, in filter-moist form, for the second substitution.

The present invention furthermore relates to a second process for the preparation of the novel N,N'-bis-1,3,5-triazin-6-ylpiperazines, wherein, in a two-step one-pot reaction, in a first reaction step, cyanuric halide, a compound XH or YH and an inorganic base are combined in the molar ratio 1:(2 to 2.2):(2 to 2.2) in the case of a monobasic base and in the molar ratio 1:(2 to 2.2):(1 to 1.1) in the case of a dibasic base, in the presence of a suspending agent at a temperature not exceeding 30° C. and at a pH of at least 5, the reaction mixture is stirred for up to 2 hours at room temperature, subsequently refluxed for 30 to 40 minutes and stirred, in a second reaction step, with piperazine and an inorganic base in the molar ratio (0.5 to 0.6):(1 to 1.2) per mol of the cyanuric halide employed in the first step in the case of a monobasic base and in the molar ratio (0.5 to 0.6) (0.5 to 0.6) per mol of the cyanuric halide employed in the first step in the case of a dibasic base, in the presence of water, refluxed for 2 to 18 hours, cooled and neutralized, and the target product is filtered off.

The second preparation process of the invention may optionally and preferably have the features that g) a phase transfer catalyst, preferably 0.1 to 1% by weight of tetra-n-butylammonium bisulfate, calculated on the basis of the cyanuric halide employed, is added to the first reaction step;

h) in the case where $X=Y=-OR^1$, the suspending agent employed is a mixture of the appropriate alcohol, phenol or naphthol R OH with water, acetone, dioxane, toluene or xylene;

i) in the case where $X=Y=-SR^1$ or $-NR^2R^3$, the suspending agent employed is water, acetone, dioxane, toluene or xylene, and the process is carried out under a nitrogen atmosphere;

j) hydroxides, bicarbonates or carbonates of alkali metals or alkaline earth metals are employed as inorganic bases;

k) a mixture of the base, the compound XH or YH, the suspending agent and, where appropriate, the phase transfer catalyst is initially introduced in the first reaction step, and cyanuric halide is added sufficiently slowly that the reaction temperature does not exceed 30° C. and the pH does not drop below 5;

l) in the reaction step, cyanuric halide is suspended in a mixture of water and ice, and the compound XH or YH and the base are stirred in sufficiently slowly that the reaction temperature does not exceed 30° C. and the pH does not drop below 5, and that the mixture is heated for up to 2 hours at 70 to 100° C. and allowed to cool.

The examples below serve to further illustrate the processes described.

EXAMPLE 1

N,N'-Bis(2,4-dimethoxy-1,3,5-triazin-6-yl)piperazine 0.5 mol of cyanuric chloride, 300 ml of acetone and 200 g of ice are mixed, and 0.25 mol of each of piperazine and $Na_2CO_3$ as 8% strength by weight and 20% strength by weight aqueous solutions respectively are added simultaneously and dropwise at minus 10° C. to 0° C. and at a pH between 5 and 7. The mixture is stirred at 0° C. for a further 30 minutes, and the solid product is filtered off and washed with water. The stillmoist filter cake is suspended in 0.2 l of methanol, and 1.05 mol of NaOH in the form of an 8% strength by weight methanol solution are added dropwise at room temperature. The reaction mixture is subsequently refluxed for 18 hours, allowed to cool and neutralized using dilute $H_2SO_4$. Finally, the product is filtered off with suction, and the residue is washed with water and dried. A finely crystalline, white powder is obtained.

Yield: 92.3% of theory
Melting point: 230°–233° C. (decomposition)
Elemental analysis: found C 45.67%; H 5.89%; N 31.19%; $C_{14}H_{20}N_8O_4$ (364.37); calc. C 46.15%; H 5.53% N 30.75%

EXAMPLE 2

N,N'-Bis(2,4-diethoxy-1,3,5-triazin-6-yl)piperazine 200 g of ice are added to 0.5 mol of cyanuric chloride in 300 ml of acetone. 0.25 mol of piperazine as an 8% strength by weight aqueous solution and simultaneously 0.25 mol of $Na_2CO_3$ as a 20% strength by weight aqueous solution are subsequently added, and the mixture is stirred for a further 30 minutes. During the reaction, a temperature of minus 15° C. to 0° C. and a pH of 5–7 are maintained. The reaction product is filtered off with suction, washed with water and, in filter-moist form, suspended in 0.2 l of ethanol. 1.05 mol of KOH in the form of a 14% strength by weight ethanol solution are then added dropwise at room temperature, and 0.1 g of tetra-n-butylammonium bisulfate is then added. The mixture is refluxed for 15 hours, during which some of the ethanol simultaneously distils off. Finally, the mixture is neutralized using dilute $H_2SO_4$, and the white, finely crystalline reaction product is filtered off with suction, washed with water and dried to constant weight.

Yield: 87.4% of theory
Melting point: 190°–193° C. (decomposition)
Elemental analysis: found C 50.95%; H 6.35%; N 27.03%; $C_{18}H_{28}N_8O_4$ (420.48); calc. C 51.42%; H 6.71%; N 26.65%

EXAMPLE 3

N,N'-Bis(2,4-dimorpholinyl-1,3,5-triazin-6-yl)piperazine

All operations are carried out in an $N_2$ atmosphere. 200 g of ice are added to 0.5 mol of cyanuric chloride suspended in 300 ml of acetone. 0.25 mol of piperazine as a 13% strength by weight aqueous solution and 0.25 mol of $Na_2CO_3$ as a 20% strength by weight aqueous solution are subsequently added dropwise simultaneously. During the addition, a temperature range of minus 16° C. to minus 8° C. and a pH of 5–7 are maintained. After the dropwise addition, the mixture is stirred for a further 30 minutes at minus 2° C. to minus 3° C. and filtered, and the filter residue is washed with water. The filter-moist reaction product is subsequently suspended in 0.2 l of water, and 1 mol of morpholine and 1.05 mol of NaOH as a 30% strength by weight aqueous solution are simultaneously added dropwise at room temperature. The reaction mixture is refluxed for 18 hours, neutralized using dilute sulfuric acid and filtered. Finally, the product is washed with water and dried to constant weight. A finely crystalline white powder is obtained.

Yield: 88.7% of theory
Melting point: 318°–321° C. (decomposition)
Elemental analysis: found C 53.06%; H 7.25%; N 29.21%; $C_{26}H_{40}N_{12}O_4$ (584.69); calc. C 53.41%; H 6.89%; N 28.75%

EXAMPLE 4

N,N'-Bis(2,4-dipiperidinyl-1,3,5-triazin-6-yl)piperazine

All operations are carried out in an $N_2$ atmosphere. 0.5 mol of cyanuric chloride is added to a mixture of 300 ml of acetone and 200 g of ice, and 0.25 mol of each of piperazine and $Na_2CO_3$ as 8% strength by weight and 20% strength by weight aqueous solutions respectively are added simultaneously. During this addition, the reaction temperature is maintained at between minus 15° C. and 0° C. and the pH is maintained at between 5 and 7. The reaction mixture is stirred for 30 minutes and filtered with suction, and the residue is washed with water and suspended in 0.2 l of water. 1 mol of piperidine and 1.05 mol of NaOH as 30% strength by weight aqueous solutions are subsequently added simultaneously dropwise at room temperature, and the mixture is refluxed for 20 hours. The reaction mixture is filtered with suction, and the residue is washed with water and dried. A finely crystalline, white powder is obtained.

Yield: 97% of theory

Melting point: 305°-307° C. (decomposition)

Elemental analysis: found C 62.08%; H 8.75%; N 29.60%; $C_{30}H_{48}N_{12}$ (576.80); calc. C 62.47%; H 8.39%; N 29.14%

EXAMPLE 5

N,N'-Bis(2,4-dimethoxy-1,3,5-triazin-6-yl)piperazine 550 ml of methanol, 55 ml of water, 0.25 g of tetra-n-butylammonium bisulfate and 1 mol of $NaHCO_3$ are mixed, and 0.5 mol of cyanuric chloride is added in portions such that the reaction temperature does not exceed 30° C. and the pH is between 5 and 8. The mixture is stirred at room temperature for 40 minutes and refluxed for 30 minutes. 0.275 mol of each of piperazine and $Na_2CO_3$ as 13% strength by weight and 20% strength by weight aqueous solutions respectively are subsequently simultaneously added dropwise at room temperature, and the reaction mixture is stirred for a further 1 hour. The mixture is then refluxed for 2 hours, allowed to cool and neutralized using dilute sulfuric acid. Finally, the mixture is filtered and the residue is washed with water and dried. A finely crystalline, white powder is obtained.

Yield: 87.2% of theory

Melting point: 229°-232° C. (decomposition)

Elemental analysis: found C 45.78%; H 5.70%; N 31.18%; $C_{14}H_{20}N_8O_4$ (364.37); calc. C 46.15%; H 5.53%; N 30.75%

EXAMPLE 6

N,N'-Bis(2,4-diethoxy-1,3,5-triazin-6-yl)piperazine 1 mol of $NaHCO_3$ and 0.5 g of tetra-n-butylammonium bisulfate are suspended in a mixture of 400 ml of ethanol and 40 ml of water, and 0.5 mol of cyanuric chloride are added in portions sufficiently slowly that the reaction temperature does not exceed 30° C. and the pH is between 5 and 8. The mixture is stirred at room temperature for a further 60 minutes and subsequently refluxed for 30 minutes. 0.275 mol of each of piperazine and $Na_2CO_3$ as 12% strength by weight and 20% strength by weight aqueous solutions respectively are then simultaneously added dropwise at room temperature, and the reaction mixture is stirred for a further 1 hour, subsequently refluxed for 3 hours and filtered at room temperature with suction, and the residue is washed with water and dried to constant weight. A finely crystalline, white powder is obtained.

Yield: 81% of theory

Melting point: 189°-193° C. (decomposition)

Elemental analysis: found C 50.98%; H 6.30%; N 27.12%; $C_{18}H_{28}N_8O_4$ (420.48); calc. C 51.42%; H 6.71%; N 26.65%

EXAMPLE 7

N,N'-Bis(2,4-dimorpholinyl-1,3,5-triazin-6-yl)piperazine

All operations are carried out under $N_2$. 1 mol of each of $NaHCO_3$ and morpholine are mixed with 0.8 l of water, and 0.5 mol of cyanuric chloride are added in portions at room temperature sufficiently slowly that the reaction temperature is 25° C. and the pH is between 7 and 10. The reaction mixture is stirred at room temperature for a further 100 minutes and refluxed for 40 minutes. 0.262 mol of each of piperazine and $Na_2CO_3$ as 13% strength by weight and 20% strength by weight aqueous solutions respectively are subsequently simultaneously added dropwise at 25° C. with stirring, and the batch is refluxed for 8 hours. The cooled reaction mixture is filtered, and the residue is washed with water and dried to constant weight. A finely crystalline, white powder is obtained.

Yield: 94.2% of theory

Melting point: 318°-321° C. (decomposition)

Elemental analysis: found C 52.92%; H 7.11%; N 29.14%; $C_{26}H_{40}N_{12}$ (584.69); calc. C 53.41%; H 6.89%; N 28.75%

EXAMPLE 8

N,N'-Bis(2,4-dipiperidinyl-1,3,5-triazin-6-yl)piperazine

All operations are carried out under a blanket of $N_2$. 1 mol of each of $NaHCO_3$ and piperidine are introduced into 0.8 l of water, and 0.5 mol of cyanuric chloride is added in portions at room temperature sufficiently slowly that the reaction temperature is 20° C. and the pH is between 7 and 11. The reaction mixture is subsequently stirred at 20° C. for a further 100 minutes and refluxed for 30 minutes. After cooling, 0.25 mol of each of piperazine and $Na_2CO_3$ as 13% strength by weight and 20% strength by weight aqueous solutions respectively are added simultaneously, and the mixture is stirred at room temperature for a further 2 hours and refluxed for 17 hours. The resultant suspension is filtered with suction, washed with water and the residue is dried to constant weight. A finely crystalline, white powder is obtained.

Yield: 93.3% of theory

Melting point: 303°-307° C. (decomposition)

Elemental analysis: found C 62.01%; H 8.87%; N 29.45%; $C_{30}H_{48}N_{12}$ (576.80); calc. C 62.47%; H 8.39%; N 29.14%

EXAMPLE 9

N,N'-Bis(2,4-dimorpholinyl-1,3,5-triazin-6-yl)piperazine

All operations are carried out under $N_2$. 0.5 mol of cyanuric chloride is suspended in a mixture of 2000 ml of water and 1000 g of ice, and 1.0 mol of morpholine and 0.5 mol of NaOH as a 10% strength by weight aqueous solution are simultaneously added dropwise. The addition is carried out sufficiently slowly that the pH is between 5 and 10. The mixture is subsequently stirred at 25° C. for a further 30 minutes, and a further 0.5 mol of NaOH as a 10% strength by weight aqueous solution is subsequently added dropwise. The reaction mixture is heated at 80° C. for 90 minutes and cooled to room temperature, and 0.28 mol of piperazine and 0.56 mol of NaOH as 10% strength by weight aqueous solutions are subsequently added dropwise. The mixture is subsequently refluxed for 12 hours and filtered at room temperature with suction, and the residue is washed with water and dried. A finely crystalline, white powder is obtained.

Yield: 98.4% of theory

Melting point: 317°–321° C. (decomposition)

Elemental analysis found C 52.94%; H 7.23%; N 28.93%; $C_{26}H_{40}N_{12}O_4$ (584.69); calc. C 53.41%; H 6.89%; N 28.75%

EXAMPLE 10

N,N'-Bis(2-ethoxy-4-morpholinyl-1,3,5-triazin-6-yl)piperazine

All operations are carried out in an $N_2$ atmosphere. 200 g of ice are added to 0.5 mol of cyanuric chloride in 300 ml of acetone. 0.25 mol of piperazine as an 8% strength by weight aqueous solution and, simultaneously, 0.25 mol of $Na_2CO_3$ as a 20% strength by weight aqueous solution are subsequently added, and the mixture is stirred for a further 30 minutes. During the reaction, a temperature of minus 15° C. to 0° C. and a pH of 5–7 are maintained. The reaction product is filtered off with suction, washed with water and, in a filter-moist form, suspended in 0.2 l of ethanol. 0.525 mol of KOH in the form of a 14% strength by weight ethanol solution is then added dropwise at room temperature, and 0.1 g of tetra-n-butylammonium bisulfate is then added. The mixture is subsequently refluxed for 10 hours, and then neutralized using dilute $H_2SO_4$, and the solid product is filtered off with suction and washed with water. The filter-moist residue is suspended in 0.2 l of water, and 0.5 mol of morpholine and 0.525 mol of NaOH as a 30% strength by weight aqueous solution are added dropwise at room temperature. The mixture is subsequently refluxed for 18 hours, neutralized using dilute $H_2SO_4$ and filtered with suction. The residue is washed with water and dried. A finely crystalline, white powder is obtained.

Yield: 85.7% of theory

Melting point: 220°–223° C. (decomposition)

Elemental analysis: found C 52.10%; H 6.41%; N 27.44%; $C_{22}H_{34}N_{10}O_4$ (502.58); calc. C 52.58%; H 6.82%; N 27.87%

EXAMPLE 11

N,N'-Bis(2,4-di-α-naphthoxy-1,3,5-triazin-6-yl)piperazine 1 mol of $NaHCO_3$ and 0.5 g of tetra-n-butylammonium bisulfate are suspended in a mixture of 1 mol of α-naphthol and 400 ml of water, and 0.5 mol of cyanuric chloride is added in portions sufficiently slowly that the reaction temperature does not exceed 30° C. and the pH is between 5 and 8. The mixture is stirred at room temperature for a further 60 minutes and subsequently refluxed for 40 minutes. 0.275 mol of each of piperazine and $Na_2CO_3$ as 12% strength by weight and 20% strength by weight aqueous solutions respectively are then simultaneously added dropwise at room temperature and the reaction mixture is stirred for a further 1 hour, subsequently refluxed for 6 hours and filtered with suction at room temperature, the residue is washed with water and dried. A finely crystalline, white powder is obtained.

Yield: 82.0% of theory

Melting point: 211°–213° C. (decomposition)

Elemental analysis: found C 72.93%; H 4.92%; N 14.25%; $C_{50}H_{36}N_8O_4$ (812.90); calc. C 73.88%; H 4.46%; N 13.78%

We claim:

1. An N,N'-bis-1,3,5-triazin-6-ylpiperazine of the formula

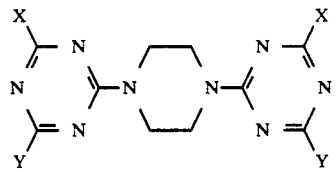

in which X and Y are identical or different radicals $-OR^1$, $-SR^1$, or $-NR^2R^3$, where $R^1$ is a $C_1$- to $C_{18}$-alkyl group, a $C_5$- to $C_{18}$-cycloalkyl group, a phenyl or naphthyl group, or a $C_7$- to $C_{18}$-aralkyl group;

$R^2$ and $R^3$, independently of one another, are a $C_1$- to $C_3$-alkyl group, a $C_5$- to $C_{18}$-cycloalkyl group, a phenyl or naphthyl group, or a $C_7$ to $C_{18}$-aralkyl group, or $-NR^2R^3$ is piperidinyl of the formula

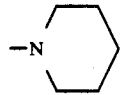

or morpholinyl of the formula

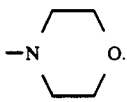

2. An N,N'-bis-1,3,5-triazin-6-ylpiperazine as claimed in claim 1, wherein $R^1$, $R^2$ or $R^3$ are a phenyl or naphthyl group which is substituted by inert radicals.

3. A process for the preparation of N,N'-bis-1,3,5-triazin-6-ylpiperazines as claimed in claim 1, which comprises, in a first reaction step, cyanuric halide, piperazine and an inorganic base reacting in the molar ratio 1:(0.5 to 0.6):(1 to 1.2) in the case of a monobasic base and in the molar ratio 1:(0.5 to 0.6):(0.5 to 0.6) in the case of a dibasic base, in the presence of water and in the presence of a further suspending agent, at temperatures of minus 20° C. to 0° C. and at a pH of 5 to 7, and filtering off the N,N'-bis(2,4-dichloro-1,3,5-triazin-6-yl)piperazine obtained as an intermediate, washing it with water and mixing it, in a second reaction step, with a compound XH or YH and an inorganic base in the molar ratio (2 to 2.2):(2 to 2.2) per mol of the cyanuric halide employed in the first reaction step in the case of a monobasic base and in the molar ratio (2 to 2.2):(1 to 1.1) per mol of the cyanuric halide employed in the first reaction step in the case of a dibasic base, in the presence of a suspending agent, refluxing the mixture for 12 to 20 hours, cooling and neutralizing it, and filtering off the target product.

4. The process as claimed in claim 3, wherein 0.01 to 0.5% by weight of tetra-n-butylammonium bisulfate, calculated on the basis of the cyanuric halide employed in the first step, are added to the second reaction step as phase transfer catalyst.

5. The process as claimed in claim 3, wherein, in the first reaction step, after addition of all the reaction components, the reaction mixture is stirred for up to 1 hour at temperatures not exceeding 0° C.

6. The process as claimed in claim 3, wherein, in the case where X or Y=$OR^1$, the suspending agent employed in the second reaction step is the corresponding alcohol, the corresponding phenol or naphthol, or a mixture thereof with water, acetone, dioxane, toluene or xylene.

7. The process as claimed in claim 3, wherein, in the case where X or Y=$SR^1$ or —$NR^2R^3$, the suspending agent employed in the second reaction step is water or mixtures of water with acetone or dioxane.

8. The process as claimed in claim 3, wherein acetone, dioxane, toluene or xylene is employed in the first reaction step as a further suspending agent.

9. The process as claimed in claim 3, wherein, in the case where X is not identical with Y, the intermediate is reacted in the second reaction step successively with the compounds XH and YH in the presence of the inorganic base in the appropriate molar ratios, the reaction product from the first substitution being filtered off, washed with water and employed, in filter-moist form, for the second substitution.

10. A process for the preparation of N,N'-bis-1,3,5-triazin-6-ylpiperazines as claimed in claim 1, which comprises, in a two-step one-pot reaction, in a first reaction step, cyanuric halide, a compound XH or YH and an inorganic base combining in the molar ratio 1:(2 to 2.2):(2 to 2.2) in the case of a monobasic base and in the molar ratio 1:(2 to 2.2):(1 to 1.1) in the case of a dibasic base, in the presence of a suspending agent, at a temperature not exceeding 30° C. and at a pH of at least 5, the reaction mixture stirring for up to 2 hours at room temperature, subsequently refluxing it for 30 to 40 minutes and stirring it, in a second reaction step, with piperazine and an inorganic base in the molar ratio (0.5 to 0.6):(1 to 1.2) per mol of the cyanuric halide employed in the first step in the case of a monobasic base and in the molar ratio (0.5 to 0.6):(0.5 to 0.6) per mol of the cyanuric halide employed in the first step in the case of a dibasic base, in the presence of water, refluxing it for 2 to 18 hours, cooling and neutralizing it, and filtering off the target product.

11. The process as claimed in claim 10, wherein 0.1 to 1% by weight of tetra-n-butylammonium bisulfate, calculated on the basis of the cyanuric halide employed, is added to the first reaction step as phase transfer catalyst.

12. The process as claimed in claim 10, wherein, in the case where X=Y=$OR^1$, the suspending agent employed is a mixture of the appropriate alcohol, phenol or naphthol $R^1OH$ with water, acetone, dioxane, toluene or xylene.

13. The process as claimed in claim 10, wherein, in the case where X=Y=$SR^1$ or —$NR^2R^3$, the suspending agent employed is water, acetone, dioxane, toluene or xylene, and the process is carried out under a nitrogen atmosphere.

14. The process as claimed in claim 10, wherein the inorganic base employed is a hydroxide, bicarbonate or carbonate of an alkali metal or alkaline earth metal.

15. The process as claimed in claim 10, wherein a mixture of the base, the compound XH or YH and the suspending agent is initially introduced in the first reaction step, and cyanuric halide is added sufficiently slowly that the reaction temperature does not exceed 30° C. and the pH does not drop below 5.

16. The process as claimed in claim 10, wherein in the first reaction step, cyanuric halide is suspended in a mixture of water and ice, and the compound XH or YH and the base are stirred in sufficiently slowly that the reaction temperature does not exceed 30° C. and the pH does not drop below 5, and wherein the mixture is heated for up to 2 hours at 70° to 100° C. and allowed to cool.

* * * * *